United States Patent [19]
Ouchi

[11] Patent Number: 6,015,381
[45] Date of Patent: Jan. 18, 2000

[54] ENDOSCOPIC TREATMENT TOOL

[75] Inventor: Teruo Ouchi, Tokyo, Japan

[73] Assignee: Asahi Kogaku Kogyo Kaisha, Tokyo, Japan

[21] Appl. No.: 09/006,166

[22] Filed: Jan. 13, 1998

[30] Foreign Application Priority Data

Jan. 17, 1997 [JP] Japan ..................................... 9-006144

[51] Int. Cl.$^7$ ....................................................... A61B 1/00
[52] U.S. Cl. ........................... 600/104; 606/205; 606/206; 606/207
[58] Field of Search ..................................... 600/104, 106, 600/564, 139, 140; 606/205, 206, 207, 170, 46

[56] References Cited

U.S. PATENT DOCUMENTS

| | | | |
|---|---|---|---|
| 4,945,920 | 8/1990 | Clossick | 606/205 X |
| 5,286,253 | 2/1994 | Fucci | |
| 5,746,696 | 5/1998 | Kondo | 600/140 X |

FOREIGN PATENT DOCUMENTS

| | | |
|---|---|---|
| 0738501 | 10/1996 | European Pat. Off. . |
| 52-40616 | 9/1977 | Japan . |
| 61-18885 | 6/1986 | Japan . |
| 9712557 | 4/1997 | WIPO . |

*Primary Examiner*—Beverly M. Flanagan
*Attorney, Agent, or Firm*—Greenblum & Bernstein, P.L.C.

[57] ABSTRACT

An endoscope treatment tool makes it possible to accurately direct a distal end driven part provided at a distal end of a sheath to a diseased part. The sheath is formed into a rotation follow-up structure such that rotation produced at its proximal end side is transmitted to its distal end side. The sheath and an operation wire are non-rotatively connected to an operation part.

16 Claims, 13 Drawing Sheets

ENDOSCOPIC TREATMENT TOOL

BACKGROUND OF THE INVENTION

This invention relates to an endoscopic treatment tool which is adapted to pass through a forceps channel of an endoscope for medical or surgical treatment.

In general, an endoscopic treatment tool such as a high-frequency snare, grip forceps, or biopsy forceps is operated such that a driven part at a distal end of a flexible sheath passing through a forceps channel is remote-controlled with an operation part provided at a proximal, operator-side end via an operation wire inserted into the sheath.

However, if the driven part is not directed to a diseased part, it is difficult to apply the treatment to the diseased part as intended. To overcome this problem, Japanese Utility Model Kokoku Publication No. Sho-61-18885 proposes a structure wherein the operation wire is arranged rotatable relative to the sheath to thereby make it possible to rotate the distal end driven part. Further, Japanese Utility Model Kokoku Publication No. Sho-52-40616 proposes a structure wherein a rotating-mechanism is incorporated to the distal end part of the sheath to thereby make it possible to control the rotative direction of the distal end driven part through a second discrete operation wire.

These proposed structures still have the following deficiencies:

In the former case, if a soft stranded wire constructed by many element wires is used as the operation wire, the rotational is not sufficiently transmitted to the distal end driven part since the operation wire dampens or absorbs the rotation. On the other hand, the use of a hard stranded wire constructed by a small number of element wires, or a single wire as the operation wire will result in improper transmission of the rotation since that wire is likely to be bent permanently (poor in flexibility).

In the latter case, the distal end driven part, in fact, cannot be rotated substantially as intended since the rotating mechanism must be added to a part where a extremely precision mechanism need inherently occupy.

SUMMARY OF THE INVENTION

An object of the present invention is to provide a novel structure for an endoscopic treatment tool, by which a driven part at a distal end of a sheath can be rotatively controlled at a proximal operator-side end as intended, to accurately direct to a disease part to be treated.

To the object, the present invention provides an endoscopic treatment tool, which includes: a flexible sheath adapted to pass through a forceps channel of an endoscope; an operation wire passing through said sheath, said operation wire being axially movable back and forth relative to said sheath; a driven part disposed at a distal end of said sheath, and connected to a distal end of said operation wire; and an operation part disposed at a proximal end of said sheath. The sheath has a rotation follow-up capability. Both of said sheath and said operation wire are non-rotatively connected to said operation part.

The sheath may include: a net pipe of braided metal wires; and a pair of synthetic resin tubes sandwiching said net pipe therebetween, or three pipes of coils closely wound one on another in different directions.

The endoscopic treatment tool may further include a thumb retaining ring provided on said operation part, said thumb retaining ring being rotatable about an axis coincident with a rotation center of said proximal end of said sheath.

The driven part may include a snare wire formed by looping a wire through which a high-frequency electric current is allowed to flow, or a forceps member operatively opened and closed.

The present disclosure relates to the subject matter contained in Japanese patent application No. 9-6144 filed on Jan. 17, 1997, which is expressly incorporated herein by reference in its entirety.

DETAILED DESCRIPTION OF ENDOSCOPIC TREATMENT TOOL

Figure 1:
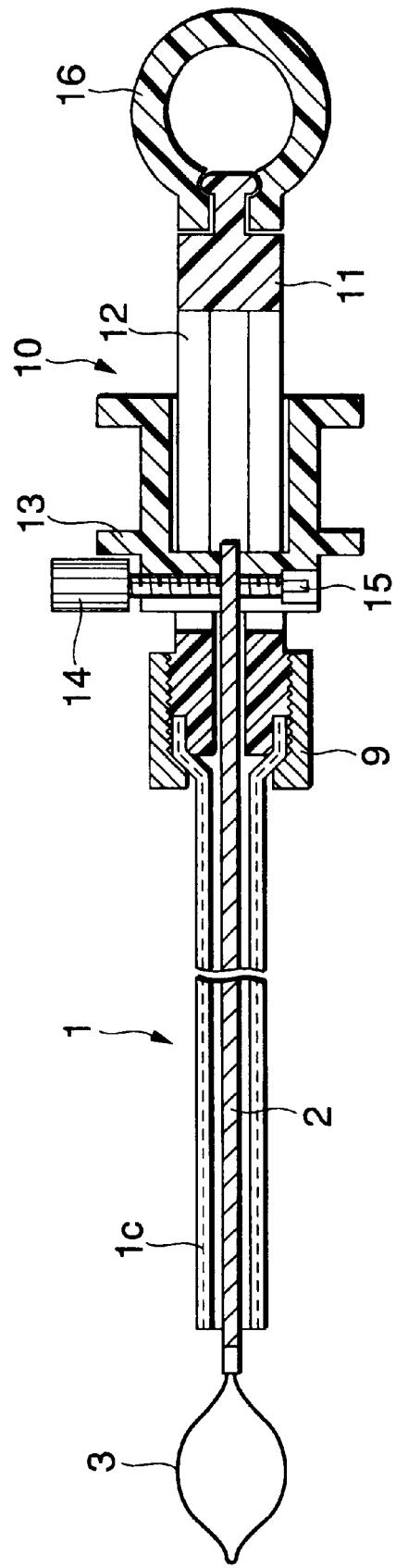
FIG. 1 is a cross-sectional side view showing an endoscopic treatment tool.
Figure 2:
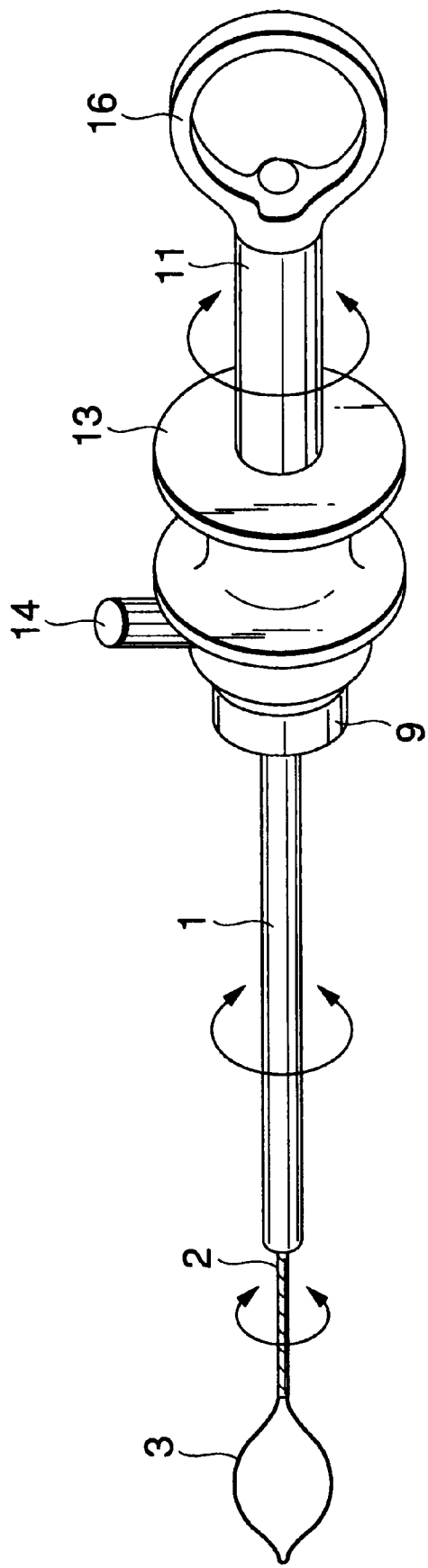
FIG. 2 is an perspective view showing the endoscopic treatment tool.

FIGS. 1 and 2 show a high-frequency snare as an example of an endoscopic treatment tool. An operation wire 2 passes through a flexible sheath 1 so as to be axially movable back and forth. The flexible sheath 1 is detachably insertable into a forceps channel of an endoscope.

Figure 3:
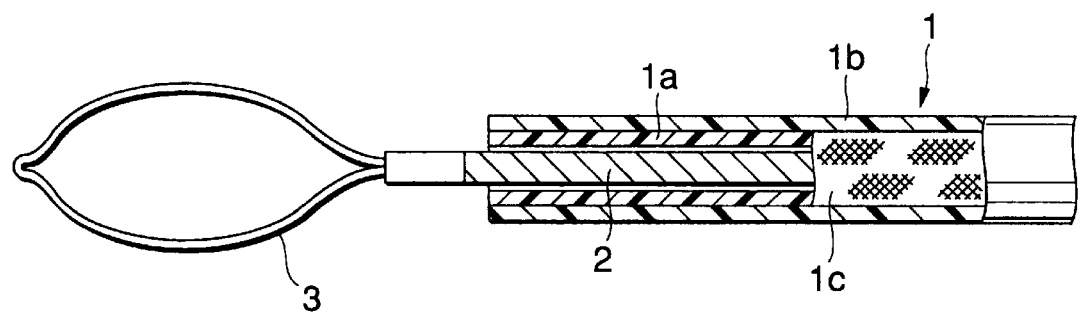
FIG. 3 is an enlarged cross-sectional side view showing the distal-end part of the endoscopic treatment tool.

The sheath 1, the cross section of which is as shown in FIG. 3, is produced in such a manner that the net pipe 1c formed by braiding fine stainless wires is incorporated and then heat-welded in between tubes 1a and 1b, with inner and outer layers, being made from synthetic resin such as tetrafluoroethylene resin.

Consequently, the sheath 1 secures not only soft and flexible property as a whole, but also has an excellent rotation follow-up capability by which rotation torque produced around the axis line at the proximal end side is sufficiently transmitted to the distal end without any substantive dampening even when the sheath is considerably long in length and bent in a meandering manner.

Figure 9:
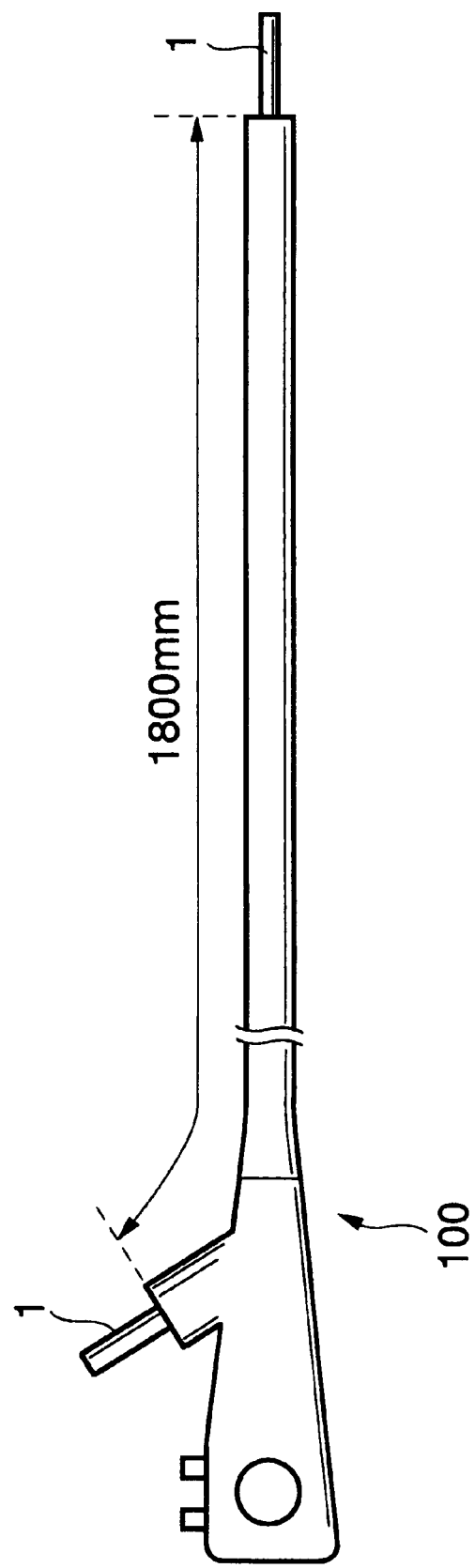
FIG. 9 is a side view showing a case where a sheath of the endoscopic treatment tool shown in FIG. 1 passes through an endoscope.

Assuming a case where the sheath 1 passes through the substantively linear forceps channel of an endoscope 100 as shown in FIG. 9 (the length between the distal and proximal ends of the forceps channel being 1,800 mm, the inner diameter of the forceps channel being 3.5 mm, and the inner wall of the forceps channel being made of PTFE), the sheath 1 is required to have such a rotation follow-up capability that the application of rotational torque of at least 100 cm-g to the proximal end side of the sheath 1 causes smooth and lag-less rotation at the distal end side of the sheath 1. That is to say, in this case, the sheath 1 is required to have the rotation follow-up capability by which the rotation torque of at least 100 cm-g produced at the proximal end side of the sheath is transmitted to the distal end of the sheath 1 without any substantive dampening.

Figure 10:
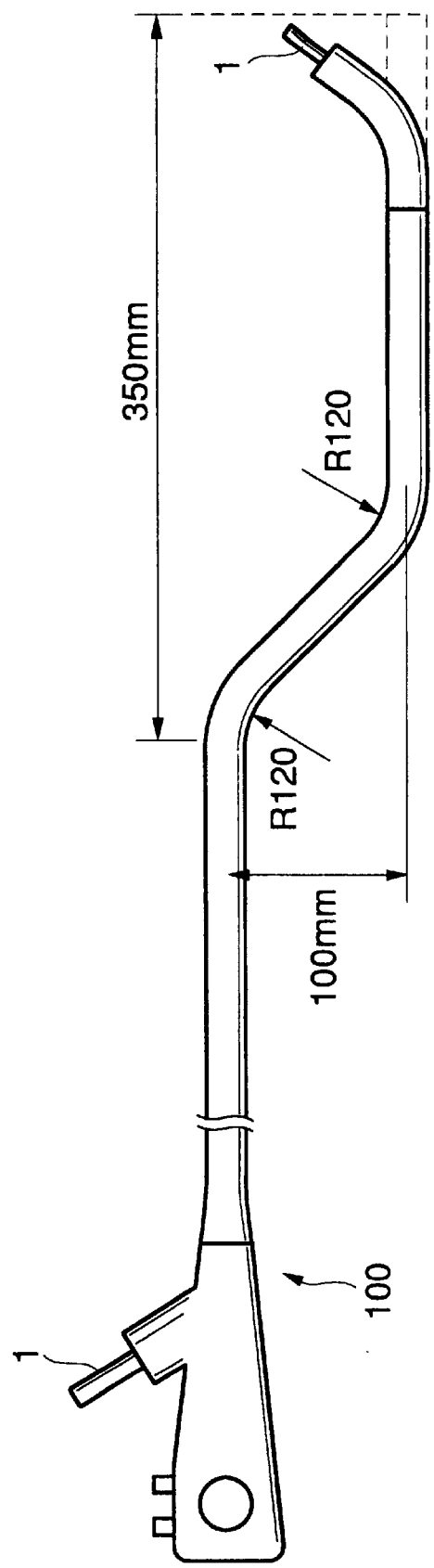
FIG. 10 is a side view showing a case where the sheath passes through the endoscope bent in a meandering manner.
Figure 11:
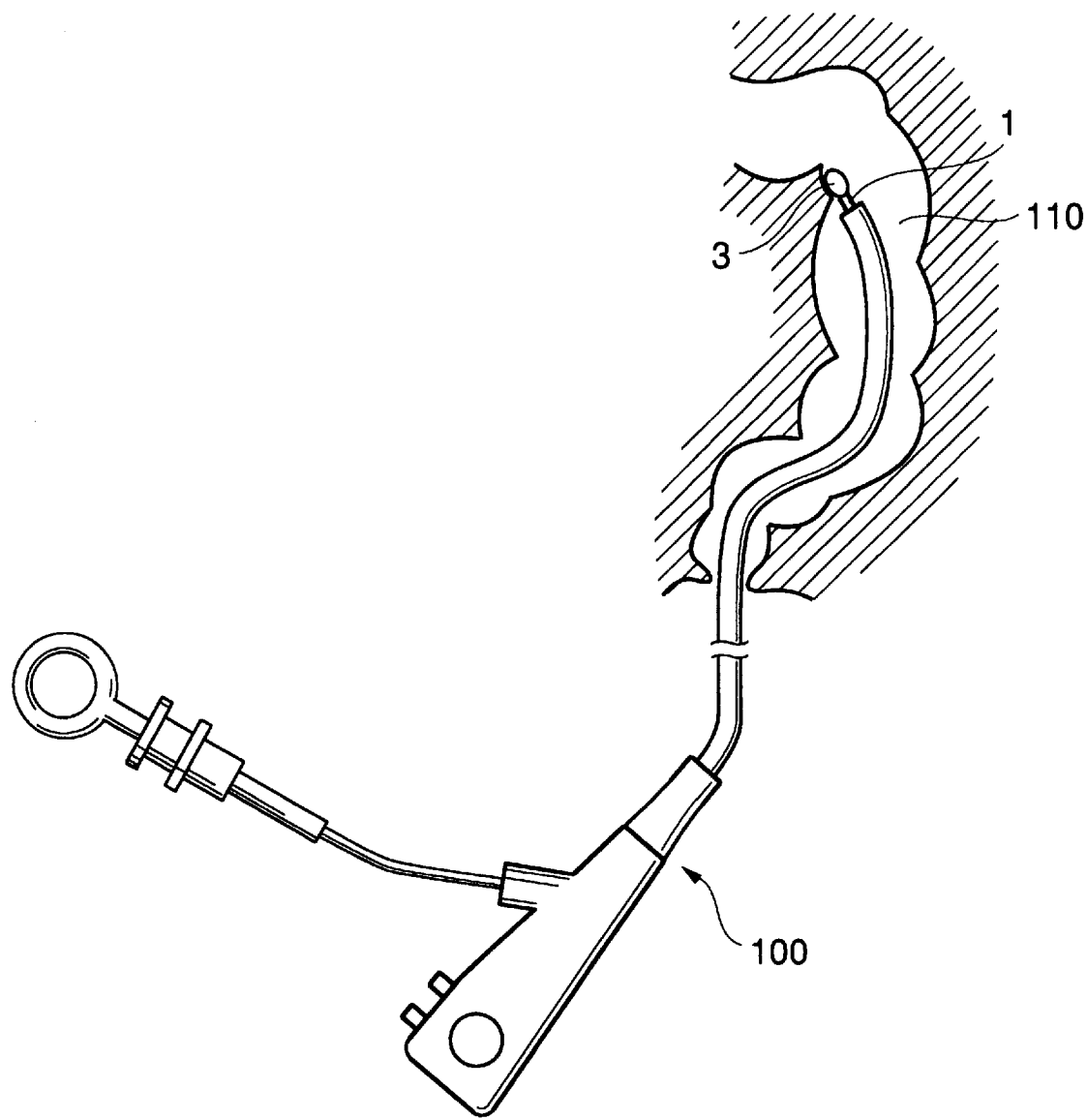
FIG. 11 is an explanatory view schematically showing the use of the endoscope for treatment in a descending colon.

Assuming another case shown in FIG. 10, which substantially simulates the use of the endoscope 100 for treatment in a descending colon 110 as shown in FIG. 11, the sheath 1 is required to have such a rotation follow-up capability that the application of rotational torque of at least 120 cm-g to the proximal end side of the sheath 1 causes smooth and lag-less rotation at the distal end side of the sheath 1.

Figure 12:
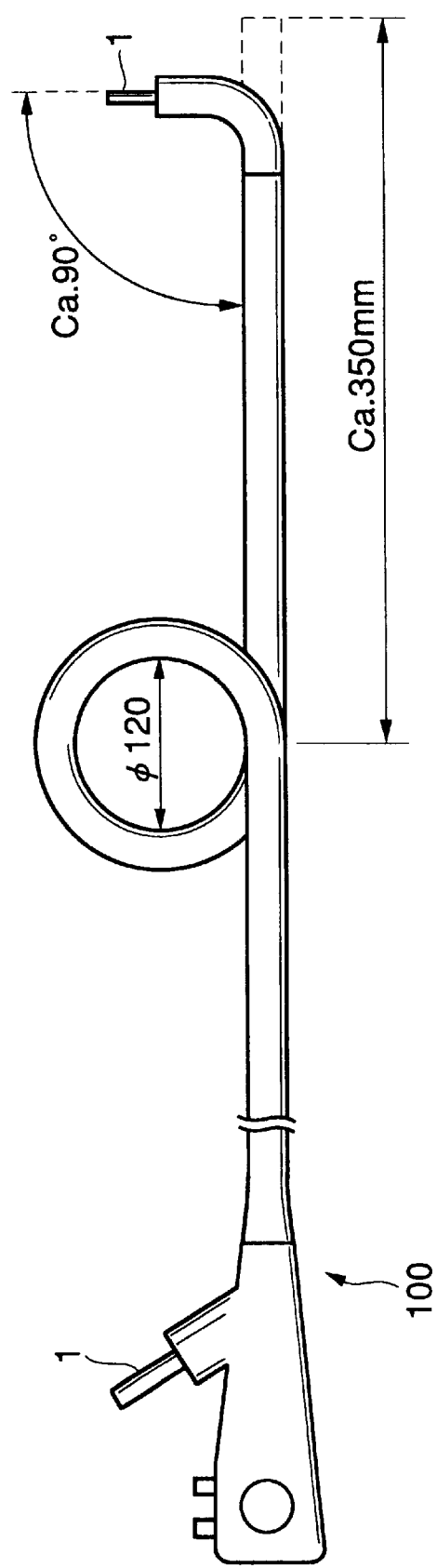
FIG. 12 is a side view showing a case where the sheath passes through the endoscope bent in fully one turn with its distal end bent at 90°.
Figure 13:
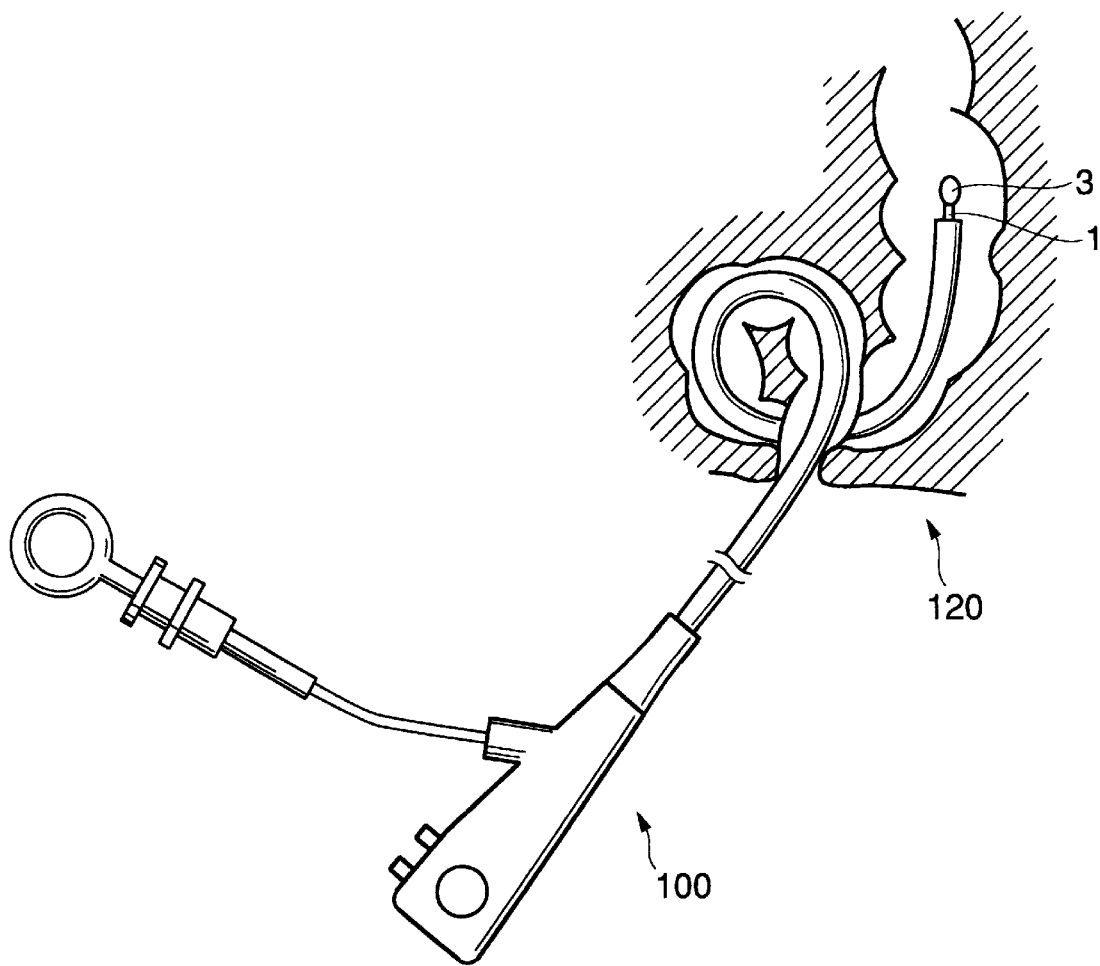
FIG. 13 is an explanatory view schematically showing the use of the endoscope for treatment in a sigmoid colon.

Assuming yet another case shown in FIG. 12, which substantially simulates the use of the endoscope 100 for treatment in or near a sigmoid colon 120 as shown in FIG. 13, the sheath 1 is required to have such a rotation follow-up capability that the application of rotational torque of at least 250 cm-g to the proximal end side of the sheath 1 causes smooth and lag-less rotation at the distal end side of the sheath 1.

To the distal end of the operation wire 2, a snare wire (a distal end driven part) 3 is connected, which is formed by looping a wire. The snare wire 3 is closed if it is pulled into the sheath by the operation wire 2, and opened to form a loop due to own elasticity when it is pushed out of the distal end of the sheath 1.

Returning to FIGS. 1 and 2, the proximal end of the sheath 1 is fixed to an operation main body 11 by means of a cap nut 9. The operation main body 11 is formed in a shape of a bar whose axis coincides with the extended line of the center line of the sheath 1. In addition, a slider 13 to which the proximal end of the operation wire 2 is fixed is engaged slidably in an elongated slit 12 formed in the operation main body 11.

Reference numeral 14 designates a cap screw for fixing the operation wire 2 to the slider 13; and 15, a connector to which a high-frequency power-supply line, which is not shown in the drawing, is connected. A portion of the screw is in contact with the operation wire 2, so that a high-frequency current is allowed to flow through the snare wire 3 via the operation wire 2.

A thumb retaining ring 16 is provided at the proximal end side (operator side) of the operation main body 11. The thumb retaining ring 16 can rotate freely about the center axis line of the operation main body 11 (i.e. the extended line of the center axis line of the sheath 1) relative to the operation main body 11.

In the high-frequency snare thus constructed, the proximal end of the sheath 1 having the rotation follow-up capability is non-rotatably fixed to the operation main body 11, whereas the proximal end of the operation wire 2 is fixed to the slider 13 engaged with the operation main body 11 through to the slit 12.

Consequently, as shown in FIG. 2, if the operation main body 11 is rotated about its axis, the snare wire 3 fixed to the distal end of the operation wire 2 as well as the sheath 1 are rotated to follow the main body 11.

Figure 4:
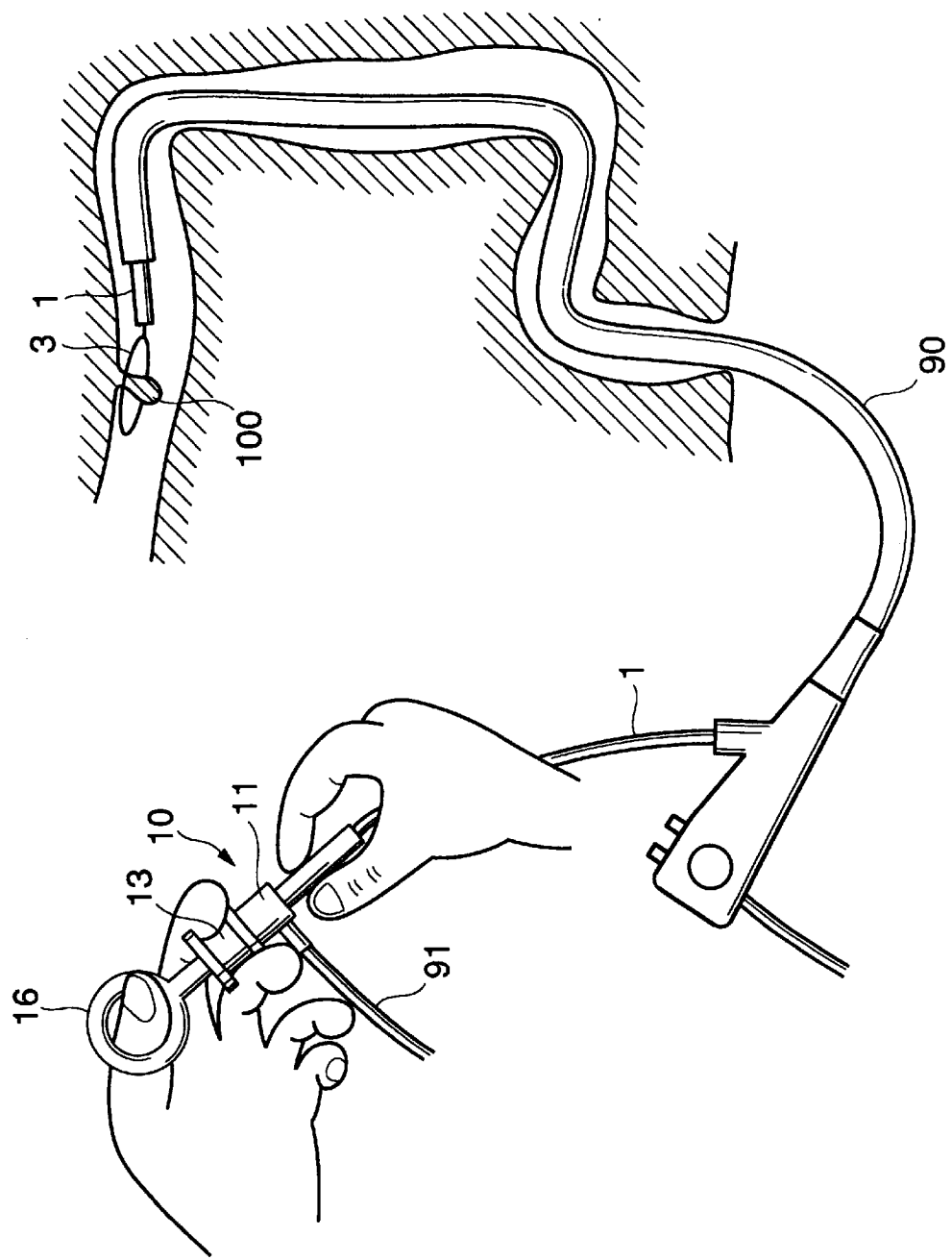
FIG. 4 is an explanatory view showing the endoscopic treatment tool under operation.

FIG. 4 shows the high-frequency snare in combination with an endoscope 90 under operation. The high-frequency snare is inserted into the forceps channel of the endoscope 90 for surgical treatment, e.g. cutting off a polyp 100 in the large intestine. Reference numeral 91 is a high-frequency power supply line.

As shown in FIG. 4, if the operator engages the thumb of his left hand to the thumb retaining ring 16 and rotates the operation main body 11 or the sheath 1 with his right hand, then the sheath 1 and the snare wire 3 are rotated following the rotation of the operation main body 11 or the sheath 1.

Therefore, adjusting the snare wire 3 to the best orientation for the polyp 100, then binding tight the polyp 100, and then allowing high-frequency current through the snare wire 3 will allow the polyp 100 to be cut off.

Figure 5:
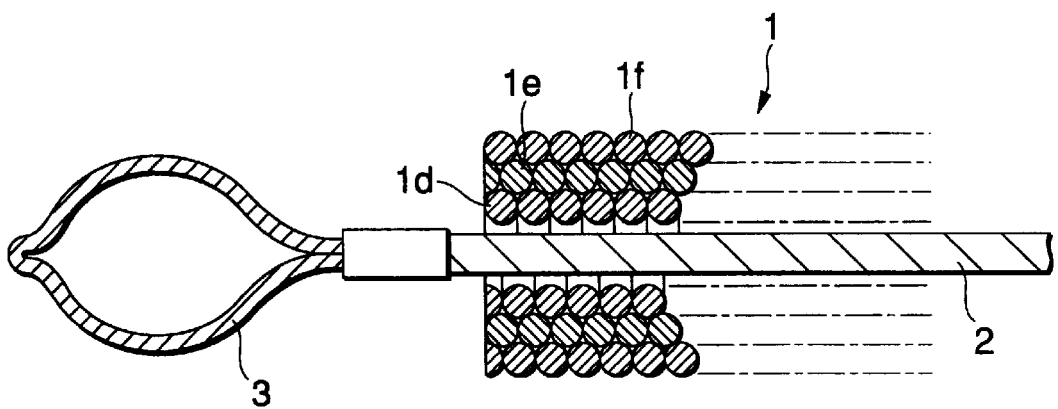
FIG. 5 is a cross-sectional side view showing a distal-end part of another endoscopic treatment tool.

FIG. 5 shows another preferable structure of the sheath 1 which has an excellent rotation follow-up capability. The sheath 1 is formed by the three layers of closely wound coil pipes 1d, 1e, and 1f, the directions of coils of which are changed alternately.

The sheath 1 may take various types of structure. For example, the outer periphery of a pipe of double spirals with each spiral being wound in different direction is covered by a net pipe, and further the outer surface of the net pipe is covered by a flexible tube.

Figure 6:
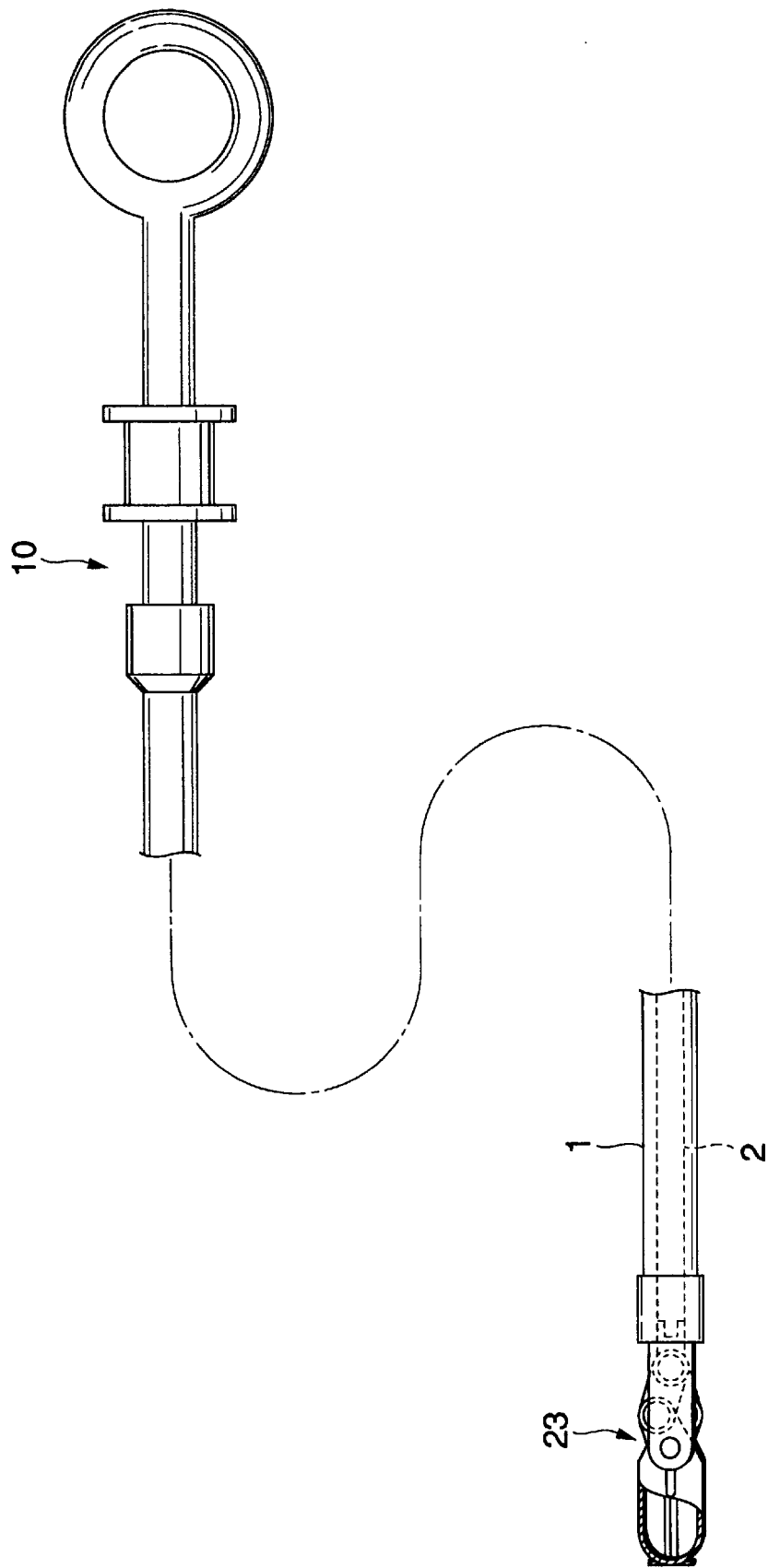
FIG. 6 is a side view showing another endoscope treatment tool.
Figure 7:
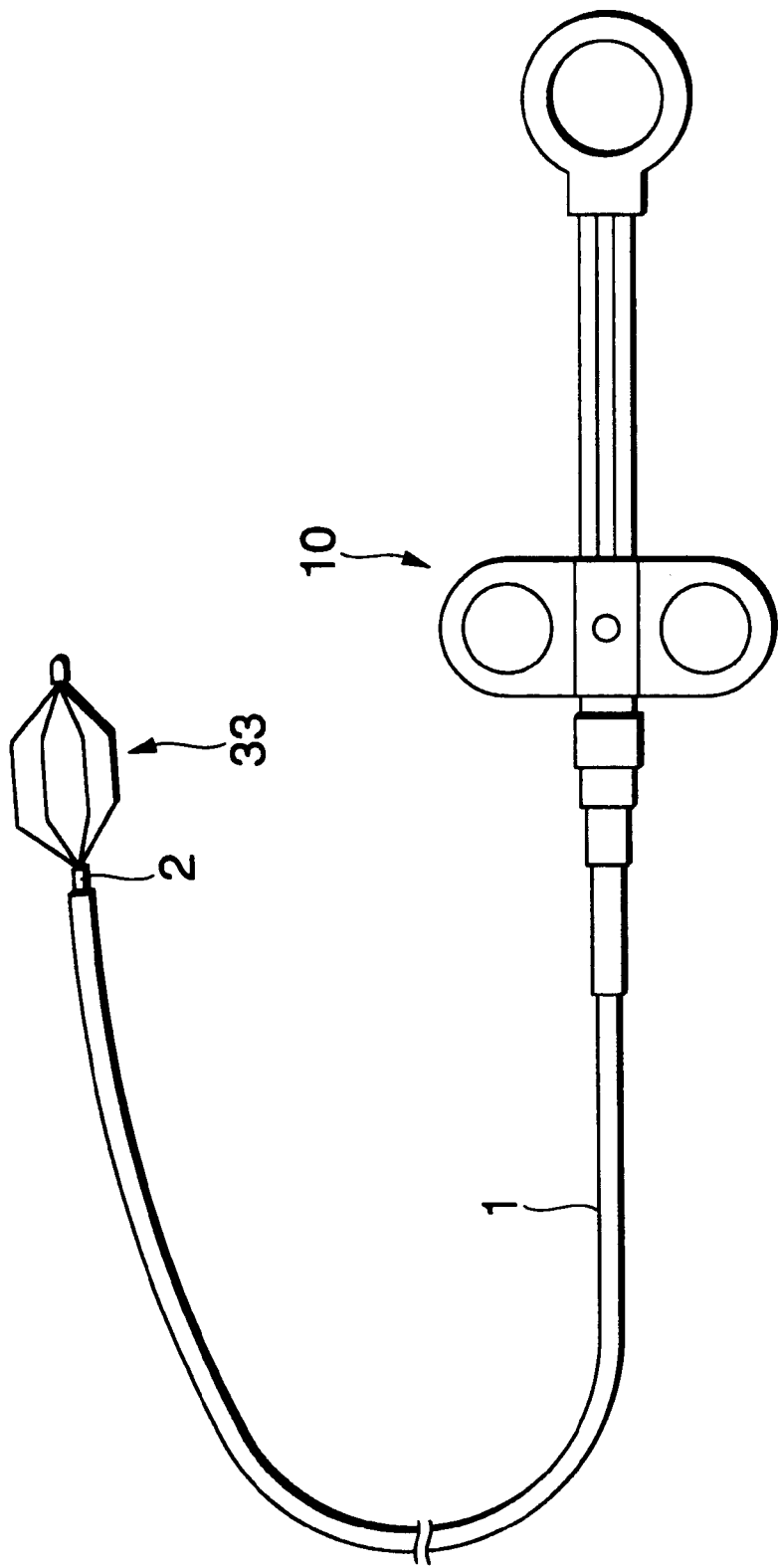
FIG. 7 is a side view showing another endoscopic treatment tool.
Figure 8:
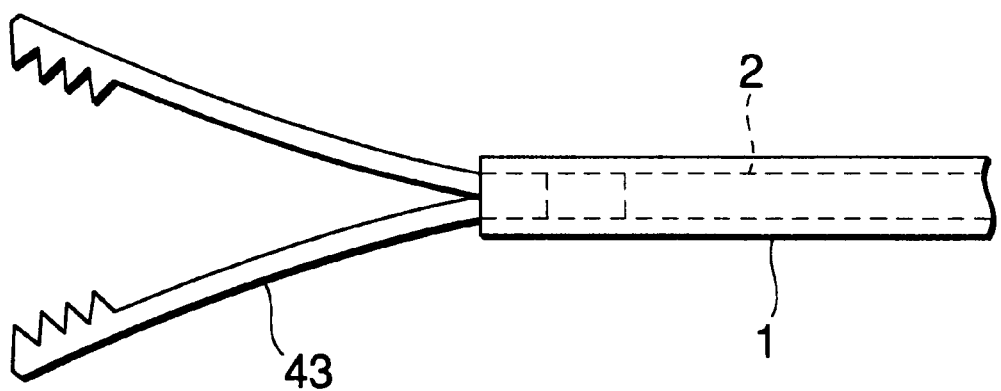
FIG. 8 is a side view showing a distal-end part of another endoscopic treatment tool.

Furthermore, the novel structure for the endoscopic treatment tool explained with reference to the high-frequency snare can be applied to various endoscopic tools, for example, a biopsy forceps as shown in FIG. 6, a basket type grip forceps as shown in FIG. 7, a beak type grip forceps for the endoscope as shown in FIG. 8, a high-frequency incision tool not shown in a drawing, and so on.

In FIG. 6, reference numeral 23 expresses the distal end driven part of the biopsy forceps, which has a forceps cup operatively opened and closed via a link mechanism by the operation wire 2. Reference numerals 33 and 43 in FIGS. 7 and 8 respectively designate the distal end driven parts of the basket type forceps and the beak type forceps, each of which is expanded due to own elasticity and contracted by being pulled into the sheath 1.

What is claimed is:

1. An endoscopic treatment tool comprising:
    a flexible sheath adapted to pass through a forceps channel of an endoscope;
    an operation wire passing through said sheath, said operation wire being axially movable back and forth relative to said sheath;
    a driven part disposed at a distal end of said sheath, and connected to a distal end of said operation wire; and
    an operation part disposed at a proximal end of said sheath,
    wherein said sheath has a rotation follow-up capability that extends through the entire length of the sheath; and
    wherein both of said sheath and said operation wire are non-rotatively connected to said operation part so that rotation of the operation part causes rotation of the driven part about an axis of the operation wire.

2. The endoscopic treatment tool as set forth in claim 1, wherein said sheath includes:
    a net pipe of braided metal wires; and
    a pair of synthetic resin tubes sandwiching said net pipe therebetween.

3. The endoscopic treatment tool as set forth in claim 1, wherein said sheath includes three pipes of coils closely wound one on another in different directions.

4. The endoscopic treatment tool as set forth in claim 1, further comprising:
    a thumb retaining ring provided on said operation part, said thumb retaining ring being rotatable about an axis coincident with a rotation center of said proximal end of said sheath.

5. The endoscopic treatment tool as set forth in claim 1, wherein said driven part includes a snare wire formed by looping a wire through which a high-frequency electric current is allowed to flow.

6. The endoscopic treatment tool as set forth in claim 4, wherein said driven part includes a snare wire formed by looping a wire through which a high-frequency electric current is allowed to flow.

7. The endoscopic treatment tool as set forth in claim 1, wherein said driven part includes a forceps member operatively opened and closed.

8. The endoscopic treatment tool as set forth in claim 4, wherein said driven part includes a forceps member operatively opened and closed.

9. The endoscopic treatment tool as set forth in claim 1, said operation part includes:

a first member to which said sheath is non-rotatively connected; and a second member to which said operation wire is non-rotatively connected, said second member being axially slidably supported by said first member.

10. The endoscopic treatment tool as set forth in claim 1, wherein said sheath has such rotation follow-up capability that in case where the sheath passes through a forceps channel of an endoscope where a length between distal and proximal ends of the forceps channel is 1,800 mm, and an inner diameter of the forceps channel is 3.5 mm, application of rotational torque of at least a predetermined magnitude to a first portion of the sheath adjacent the proximal end of the forceps channel causes smooth and lag-less rotation at a second portion of the sheath adjacent the distal end of the forceps channel.

11. The endoscopic treatment tool as set forth in claim 10, wherein said predetermined magnitude is not less than 100 mm-g.

12. The endoscopic treatment tool as set forth in claim 11, wherein said predetermined magnitude is not less than 120 mm-g.

13. The endoscopic treatment tool as set forth in claim 12, wherein said predetermined magnitude is not less than 250 mm-g.

14. An endoscopic treatment tool comprising:

a flexible sheath adapted to pass through a forceps channel of an endoscope;

an operation wire passing through said sheath, said operation wire being axially movable back and forth relative to said sheath;

a driven part disposed at a distal end of said sheath, and connected to a distal end of said operation wire; and an operation part disposed at a proximal end of said sheath, wherein said sheath is constructed by at least three pipes formed by closely winding coils one on another in different directions, and wherein both said sheath and said operation wire are non-rotatively connected to said operation part and wherein said sheath has a rotation follow-up capability that extends through the entire length of the sheath so that rotation of the operation part causes rotation of the driven part about an axis of the operation wire.

15. The endoscopic treatment tool as set forth in claim 1, wherein the driven part is movable in a longitudinal direction relative to the distal end of the sheath.

16. The endoscopic treatment tool as set forth in claim 14, wherein the driven part is movable in a longitudinal direction relative to the distal end of the sheath.

* * * * *